United States Patent [19]

Shackelford et al.

[11] Patent Number: 4,551,249

[45] Date of Patent: Nov. 5, 1985

[54] MODULAR LIQUID CHROMATOGRAPHY COLUMN APPARATUS

[75] Inventors: Carl L. Shackelford, San Pablo; Kenneth Rainin, Piedmont, both of Calif.

[73] Assignee: Rainin Instrument Co. Inc., Emeryville, Calif.

[21] Appl. No.: 584,611

[22] Filed: Feb. 29, 1984

[51] Int. Cl.⁴ .............................................. B01D 15/08
[52] U.S. Cl. ................................... 210/198.2; 55/386
[58] Field of Search ........................ 210/198.2; 55/386

[56] References Cited

U.S. PATENT DOCUMENTS

| | | | |
|---|---|---|---|
| 4,026,803 | 5/1977 | Abrahams et al. | 210/198.2 |
| 4,280,905 | 6/1981 | Gunkel et al. | 210/198.2 |
| 4,283,280 | 8/1981 | Brownlee | 210/198.2 |
| 4,313,828 | 2/1982 | Brownlee | 210/198.2 |
| 4,389,313 | 6/1983 | Charney et al. | 210/198.2 |

OTHER PUBLICATIONS

Altex Chromatography Columns, a Publication of Altex Scientific Co., Berkley, Calif., pp. 2–8, no date.

Primary Examiner—John Adee
Attorney, Agent, or Firm—Bielen and Peterson

[57] ABSTRACT

A chromatography column apparatus which utilizes sorbant material in a tube which has a first and second end portion. The first end portion of the tube includes a plug having a passage through the same. The plug fits in the same, adjacent the sorbant material, and is movable within the tube. An end fitting is also employed which has a portion that is placed within the tube adjacent the plug. The end fitting has a passage therethrough which communicates with the passage of the plug. A seal is used inside the tube between the plug and the end fitting. The end fitting and plug are held together. The second end portion of the tube is enclosed and also includes a passage from the interior to the exterior of the tube.

16 Claims, 4 Drawing Figures

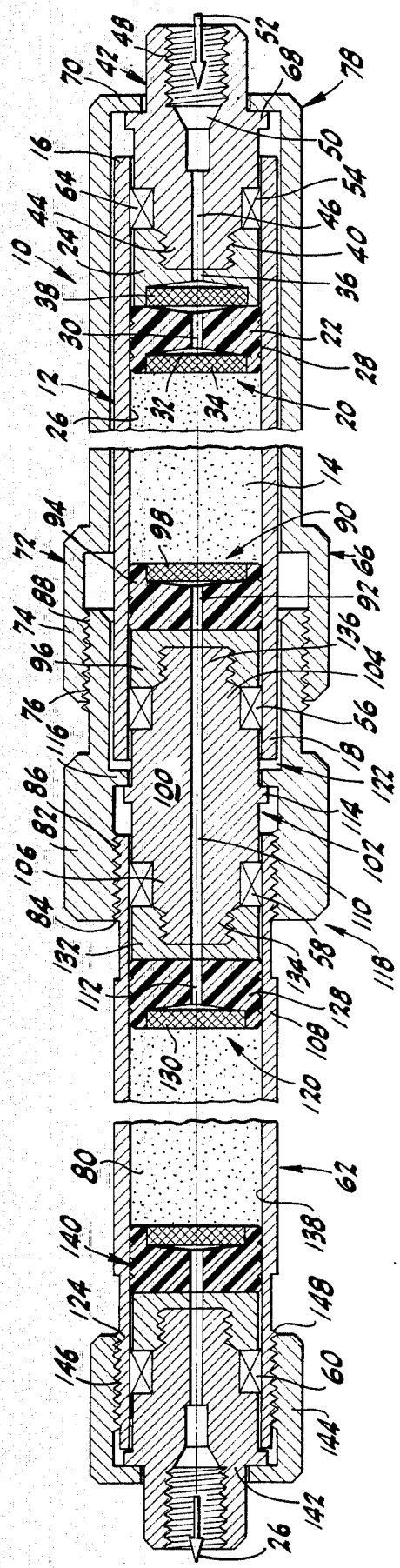
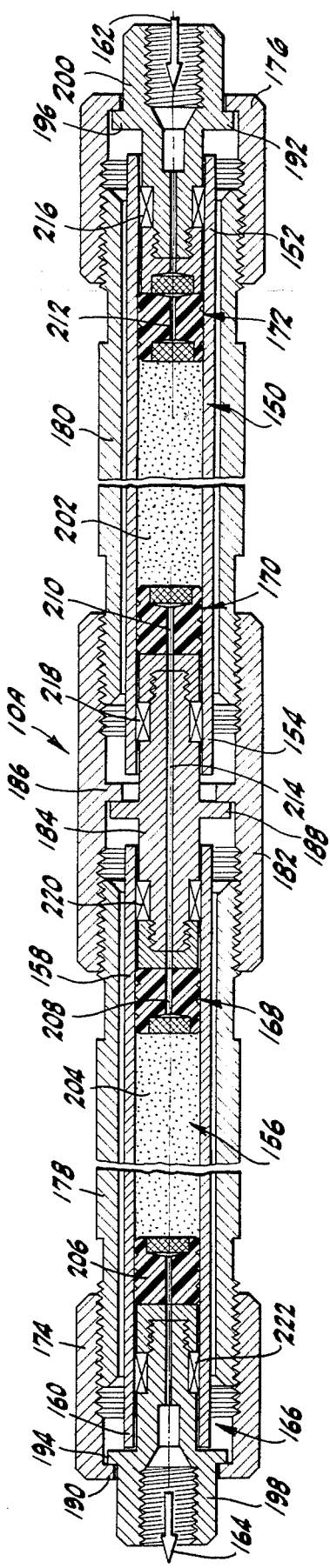
FIG-1
FIG-2

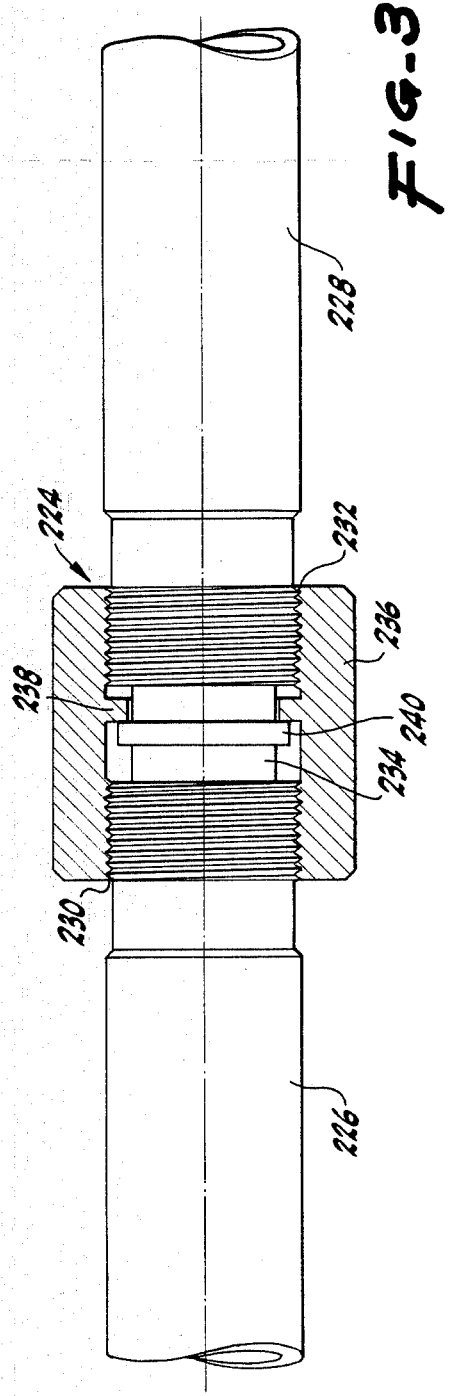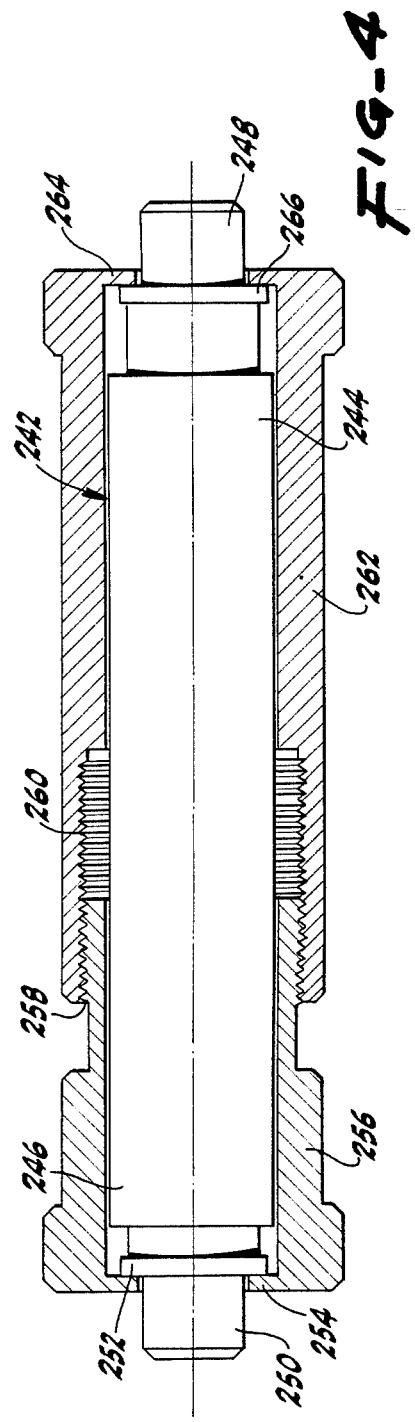

MODULAR LIQUID CHROMATOGRAPHY COLUMN APPARATUS

BACKGROUND OF THE INVENTION

The present invention relates to a novel and useful liquid chromatography column apparatus which has a modular function. High pressure liquid chromatography techniques utilize pumps which have a pressure pulsation as a delivery characteristic. This pulsation has a tendency to disturb packing material in a liquid chromatography column. In particular, a void may develop at the top or head of the column where most of the separation occurs. Also "Channels" may develop at the interface of the packing material and the column wall. This deterioration is reinforced by chemical attack, high temperatures and other factors. In this regard, the initial packing of a column may also create discontinuities in a portion of the packed material.

Moreover, high pressure liquid chromatography columns encounter other problems in the form of difficulties in sealing a column against leakage. Conventional seals such as those marketed under the trademark "SWAGELOK" rely on metal to metal contact and metal deformation. These seals require the use of special tools to tighten the column and the expensive end fittings needed therewith are not reuseable. In this regard, U.S. Pat. No. 4,283,280 describes a cartridge type column which employs a sealing mechanism which may be hand tightened. U.S. Pat. No. 4,313,828 describes incorporation of a seal distributed under the trademark "BAL-SEAL" into the cartridge type column described in U.S. Pat. No. 4,282,280. The liquid chromatography systems described in these patents do not apply pressure to the packing material while maintaining seal integrity.

A liquid chromatography system which solves the hereinabove mentioned problems would be a great advance in the field of liquid chromatography equipment.

SUMMARY OF THE INVENTION

In accordance with the present invention a novel and useful modular liquid chromatography column apparatus is provided which solves several problems encountered in the prior art.

The high pressure modular liquid chromatography column apparatus of the present invention employs a tube, which may be a first tube, filled with material used for separating constituents. The tube has a first end portion and second end portion. Means is provided for plugging the first end portion of the tube and is placed adjacent the packing material. The plugging means or seal retainer includes a passage through the same which serves as an inlet to the packing material for the solution being analyzed. The plugging means is movable within the tube and is therefore capable of pressing against the packing material therewithin. The plugging means may take the form of a stopper which is movable within the tube and a seal retainer adjacent the stopper. Both the seal retainer and the stopper would include passages therethrough for the transportation of the solution from the exterior of the tube to the packing material. The stopper and seal retainer may include filters which aid in the purification of these solutions being analyzed before contact with the packing material in the tube. Such filters also tend to properly distribute the solution across the head of the packing material.

The column apparatus structure also provides for an end fitting which has a portion placed within the tube adjacent the plugging means. The end fitting includes a passage through the same which communicates with the passage of the plugging means e.g., the passages of the stopper and seal retainer.

The invention contemplates means for sealing a portion of the inside of the tube between the plugging means and the end fitting. The sealing means may lie between the seal retainer and the end fitting may be itself movable along the inside of the tube. Such movement may take place in conjunction with the movable stopper. Means may also be included for connecting the portion of the plugging means to the end fittings. In certain cases, the end fitting may threadingly engage a threaded portion of the seal retainer. Likewise, the column apparatus may embrace means for holding the end fitting to the plugging means and/or urging the end fitting against the plugging means. This element would permit pressure to be exerted against the packing material by the stopper and also effect operation of the sealing means to prevent leakage of the solution from the inside of the tube.

The second end portion of the tube may be enclosed by appropriate means and include a passage therethrough which may serve as the outlet of the first tube of the column apparatus.

A second tube may be used in conjunction with the first tube. The second tube may be filled with material and have first and second end portions. Each end portion of the second tube may include means for enclosing the same. A coupler which possesses an element may interconnect the first and second tubes. The coupler element includes a first and second portion such that the first portion fits within and is movable within the second end portion of the first tube. Similarly the coupler element second portion fits within and is movable within the first end portion of the second tube. The second tube has a structure which provides first and second passages through the first and second closing means respectively which communicate with material in the second tube. The coupler element also is provided with a passage therethrough which communicates with the first passage of the first enclosing means of the first end portion of the second tube and with the second passage of the second enclosing means of the second end portion of the first tube. A coupler structure may also require means for holding first and second portions of the coupler elements to the first enclosing means of the first end portion of the second tube and to the enclosing means of the second end portion of the first tube. Means for urging the coupler element against the enclosing means of the second end portion of the first tube may also be included. Such means may be connected to the means for urging the first end fitting of the first tube against the plugging means. In fact, the enclosing means of the first and second tubes are being squeezed toward one another creating pressure on the packing within the first and second tubes.

It may be apparent that a novel and useful modular liquid chromatography column apparatus has been described.

It is therefore an object of the present invention to provide a high pressure liquid chromatography column (HPLC) apparatus which may be hand tightened and loosened without the need for tools and which provides for reusing end fittings supplied for this purpose.

Another object of the present invention is to provide an HPLC column apparatus which applies pressure directly to the packing material within the column apparatus to correct any voids or channels which may be present in the column after the initial packing or which may develop after use of the column apparatus.

It is yet another object of the present invention to provide an HPLC column apparatus which eliminates metal deformation as a process for sealing the column apparatus.

It is still another object of the present invention to provide an HPLC column apparatus which incorporates the seals and the pre-filters within the tubular bodies of the apparatus.

It is another object of the present invention to provide an HPLC column apparatus which possesses a relatively small dead volume.

Another object of the present invention is to provide an HPLC column apparatus which permits the coupling of a pre-column or guard column to a separation column or the coupling of a plurality of separation columns together and to provide for the application of mechanical pressure to the packing materials in both tubular columns.

It is another object of the present invention to provide an HPLC column apparatus which is useful in the analytical semi-preparative and preparative liquid chromatography separation processes.

It is yet another object of the present invention to provide an HPLC column apparatus which minimizes the need for peripheral hardware thus reducing the overall cost of the HPLC apparatus.

It is yet another object of the present invention to provide an HPLC column apparatus having a replaceable filter element within a packed column which prevents fouling and disposal of the same.

The invention possesses other objects and advantages especially as concerns particular characteristics and features thereof which will become apparent as the specificaton continues.

BRIEF DESCRIPTION OF THE DRAWINGS

FIG. 1 is a sectional view having broken portions of an embodiment of the column apparatus of the present invention.

FIG. 2 is a sectional view having broken portions of an embodiment of the column apparatus of the present invention.

FIG. 3 is a sectional view partially in elevations showing a coupling of two tubes.

FIG. 4 is a sectional view partially in elevation showing a single packed tube the packing material of which may be axially compressed.

For a better understanding of the invention reference should be made to the following detailed description of the preferred embodiments thereof which should be taken in conjunction with the hereinabove drawings.

DESCRIPTION OF THE PREFERRED EMBODIMENTS

Various aspects of the present invention will evolve from the following detailed description of the preferred embodiment which should be referenced to the hereinabove described drawings.

The invention as a whole is shown in the drawing by reference character 10 and 10A. The column apparatus 10A, FIG. 1, includes as one of its element a tube 12 which is filled with packing material 14 normally used in liquid chromatography separations. For example silica gel, and the like. Tube 12 may be constructed of relatively rigid material such as stainless steel, aluminum, and the like. Tube 12 includes the first end portion 16 and a second end portion 18. Means 20 is provided for plugging first end portion of said tube. Plugging means may include a stopper 22 and a seal retainer 24 in side-by-side configuration. Stopper 22 may exert pressure on packing material 14 by direct contact. Both stopper 22 and seal retainer 24 are movable along the inside surface 26 of tube 12.

Stopper 22 may be constructed of a plastic material and include a series of grooves or striations 28 on its outer surface. A passage 30 also exists to allow liquid to travel therethrough. Passage 30 flares into an open chamber 32 which contains a filter 34 in the form of a frit which filters and distributes liquid passing therethrough. Seal retainer 24 also includes a passage and open chamber combination 36 which holds a frit filter 38 adjacent seal retainer 24. Frit 38 is easily replaceable. Seal retainer 24 may be constructed and formed of metallic material such as stainless steel, aluminum, and the like. End fitting 42 includes a threaded 44 which threadingly engages threaded hollow 40 of seal retainer 24. Thus, seal retainer 24 and end fitting 42 may be locked together as a unit. Seal retainer also includes a passage 46 which leads from a threaded opening 48 to a reducing chamber 50 and to short passage 36 of seal retainer 24. Thus, liquid being analyzed by the apparatus 10A would flow according to arrow 52. Leakage from the inside of tube 12 is controlled by seals 54 and 56 (shown schematically). Tube 62, which will be more fully described hereinafter, utilizes seals 58 and 60, FIG. 1. Seals 54, 56, 58 and 60 may be a spring loaded Teflon and Teflon compounded seal manufactured under the name "BAL-SEAL" by the Bal-Seal Engineering Company of Santa Ana, Calif., Series U-300 for static conditions. Sealing means 54 seals a portion of the inside surface 26 of tube 12 between plugging means 20 and end fitting 42 specifically. By way of example, sealing means 54 occupies the torroidal chamber 64 formed by the end fitting 42, seal retainer 24, and the inside surface 26 of tube 12.

FIG. 1 also depicts means 66 for retaining end fitting 42 within tube 12. Such means may take the form of rim 68 on seal retainer 42 which contacts collar 70 of coupling means 72 for linking first tube 12 to second tube 62. Coupling means 72 may take the form of a generally cylindrical member 74 having a threaded end portion 76 as well as the heretofore described collar 70.

The column apparatus 10 also includes in one of its embodiments means 78 for urging end fitting 42 against plugging means 20. Such means 78 would create axial compression along tubes 12 and 62, which would in turn compress the packing material 14 in tube 12 and the packing material 80 in tube 62. Means 78 would combine coupling means 72 with end cap 82 and the threaded end portion 84 of second tube 63. The internally threaded portion 86 of end cap 82 threadingly engages threaded end portion 84 of tube 62. In addition, the externally threaded portion 88 of end cap 82 threadingly engages the threaded end portion of cylindrical member 84.

First tube 12 possesses means 90 for enclosing second end portion 18. Means 90 includes a passage 92 therethrough to permit a flow of liquid from packing material 14. As may be observed from FIG. 1, means 90 include a stopper 94 and seal retainer 96 positioned adjacent to one another and movable along the inside surface of tube 12. Stopper 94 includes a frit filter 98.

Column apparatus 10A includes a coupler or coupler means 100 to lead first tube 12 to second tube 62 and maintain the axial compression of the packing material 14 and 80 in tube 12 and 62 respectively. Coupler 100 may include an element 102 which has a first portion 104 and a second portion 106. First portion 104 and second portion 106 of element 102 fit within second portion 18 of tube 12 and first portion 108 of second tube 62 respectively. Thus, forces exerted by means 78 would be received by element 102. Element 102 also provides a portion of the chambers housing seals 56 and 58 of first and second tubes 12 and 62. Element 102 is structured to include a passage 110 therethrough which communicates with passage 92 of enclosing means 90 and the passage 112 found in second tube 62 which will be discussed hereinafter. Element ring 114 provides a place of contact with ring 116 of end cap 82. These contacting rings in conjunction with the threading engagement between end cap 82 and threaded end portion 84 of second tube 62 results in means 118 for urging coupler element 102 against the first enclosing means 120 of first end portion 108 of second tube 62. In addition, the threaded connection between end cap 82 and cylindrical member 74 functions as means 122 for retaining element 102 within the second end portion 18 of first tube 12 and the first end portion 108 of second tube 62.

Again, with reference to FIG. 1, second tube 62 is constructed with a first end portion 108 and a second end portion 124. Packing material 80 fills the inside of second tube 62. First end portion 108 of second tube 62 includes enclosing means 118 having passage 112 therethrough which has been previously described. Enclosing means 118 may externalize in a stopper 128 having a frit filter 130 on the packing side thereof. Stopper 128 may be of similar construction to stopper 22. Retainer 132 threadingly engages the threaded boss 134 of second portion 106 of element 102. Likewise threaded boss 136 of first portion 104 of element 102 threadingly engages seal retainer 96 found in second portion 18 of first tube 12. Stopper 128 and seal retainer 132 are movable along the inside surface 138 of second tube 62. Second end portion 124 of second tube 62 also includes enclosing means 140 which will not be described in details since it is essentially identical to first enclosing means 118 of first portion 108 of second tube 62, with its elements being in reverse order. End fitting 142, and second enclosing means 140 are held within second tube 62 by end cap 144. Threaded portion 146 of end cap 144 threadingly engages the threaded end portion 148 of second tube to achieve this end. Tube 62 may also be fitted within components similar to end fitting 142 and end cap 144 at its first end portion 108. Thus, a column would be formed having axial compression exerted by tightening of end cap 144 and another end cap similar to end cap 144 at second end portion 124 and first end portion 108 of second tube 62. Such compression would tend to compress packing material 80 in the middle portion of second tube 62.

Turning to FIG. 2, another embodiment 10A of column apparatus is depicted. Column apparatus 10A includes a first tube 150 having a first end portion 152 and a second end portion 154. A second tube 156 is also provided having a first end portion 158 and a second end portion 160. Liquid is intended to flow through column apparatus 10A starting at inlet arrow 162 and exiting at outlet arrow 164. Returning to FIG. 1 and with reference to the second enclosing means 140 of the second end portion 124 of tube 62, it may be seen that a similar enclosing means 166 is used on the second end portion 160 of second tube 156. Similarly, first enclosing means 118 of end portion 108 of tube 62 is similar to closing means 168 for the first portion 158 of tube 156. Enclosing means 90, plugging means 20, and end fitting 22 of first tube 12 are also comparable to enclosing means 170 and 172 of first tube 150. It may be observed that tubes 150 and 156 are of a smaller diameter than tubes 12 and 62 of FIG. 1. Also, tubes 150 and 156 do not include threaded external portions. End caps 174 and 176 threadingly engage bushing 178 and 180. Bushing 182 threadingly engages bushings 178 and 180 a coupling element 184 extends into tubes 150 and 156 and threadingly engages enclosing means 168 and 170. An internal flange 186 of bushing 182 contacts the ring or collar 188 of coupling element 184 to urge the same toward a second tube 156. End caps 174 and 176 also includes collars 190 and 192 which engage flanges 194 and 196 of end fittings 198 and 200 respectively. Since enclosing means 156, 168, 170 and 172 are movable along the inside of tubes 150 and 156, the tightening of end caps 174, 176, or bushing 182 will cause axial compression along tubes 150 and 156 which are in end configuration. Such compression will also exert a force on packing material 202 and 204 of columns 150 and 156. Passages 206, 208 and 210 and 212 of enclosing means 166, 168, 170 and 172 permit the flow of fluid being analyzed to the packing material 202 and 204. In addition, passage 214 of coupling element 184 links the flow of liquid between first column 150 and second column 156.

Turning to FIG. 3 coupling means 224 is illustrated for the purpose of connecting tubes 226 and 228. Tubes 226 and 228 includes threaded end portions 230 and 232 similar to the threaded end portion 84 of tube 62, FIG. 1. A coupler element 234 extends to the interior of tubes 226 and 228 much in the same manner as coupler element 100 extends into tubes 12 and 62, FIG. 1. Bushing 236 possesses an internal ring or collar 238 which engages the flange or ring 240 around coupler element 234. Tubes 226 and 228 may include enclosing means similar to enclosing means 118 of the first end portion 108 of tube 62, in abuttment with either end of coupler element 234. A similar enclosing means may also be provided at the other ends of tubes 226 and 228 (not shown).

With reference to FIG. 4 a single tube 242 is depicted having unthreaded end portions 244 and 246. End fittings 248 and 250 partially fit within end portions 244 and 246 and are similar in construction to end fitting 42 associated with tube 12, FIG. 1. Also, enclosing means such as enclosing means 72 of first end portion 152 of tube 150, FIG. 2, may be found within tube 242 at first and second end portions 244 and 246. Tube 242 would also be filled with packing material such as packing material 202 which is found within tube 150, FIG. 2. Rim 252 of end fitting 250 is engaged by the flange 254, of end cap 256. End cap 256 also includes a threaded portion 258 which is threadingly engaged by threaded end portion 260 of end cap 262. Again, flange 264 of end cap 262 engages rim 266 of end fitting 248. Thus, the tightening of end caps 256 and 262 will cause end fittings 248 and 250 to actually compress the packing material within tube 242 (not shown).

In operation, the user connects column 12 to column 62, FIG. 1 by use of coupling means 100. The enclosing means on both end of either tube are inserted. End cap 144 and cylindrical member 74 are tightened against end fitting 142 and 42 respectively to compress the items found within tubes 12 and 62. Liquid is directed into the column apparatus 10 accordingly to directional arrow 52 and exists from the same toward directional arrow 126. Separation of the components takes place within the packed areas 14 and 80 of columns 12 and 62.

Similarly column apparatus 10A is assembled and tightened using end caps 174 and 176 and bushing 182. Liquid is then directed according to directional arrow 162 into column apparatus 10A and exists at directional arrow 164. Again, separation is believed to take place in the packed areas 202 and 204 of first column 150 and 156.

The exertion of axial compression in either the embodiment 10 showing in FIG. 1 or 10A in FIG. 2 will also effect the sealing of the tubes. For example tubes 12 and 62 would be sealed against leakage from within at seals 54 and 56, and at seals 58 and 60 respectively. Column apparatus 10A would seal both tubes at seal areas 216, 218, 220 and 222 (shown schematically). Seals employed in columns apparaus 10A would be similar to those employed in column apparatus 10. The tightening hereinabove described may be employed without the use of tools; in other words the apparatuses 10 and 10A may be hand tightened. It has been found that fluids under a pressure in excess of six thousand pounds per square inch (422 kg. per square centimeter) may flow through the apparatus of the present invention without leakage therefrom.

It is also possible to link other columns or tubes to the two column embodiment shown in FIGS. 1 and 2. For example, FIG. 3 represents the linking of two tubes 226 and 228 together. By merely substituting tube 62 for tube 228 three tubes may be linked together in series, namely tubes 12, 62 and 226. This may be desirable in certain liquid chromatography separation processes.

With reference to FIG. 4 it may be seen that a single tube, which may be a pre-column or guard column, also enjoys axial compression of the packing material therewithin. By simply tightening end caps 256 and 262 such axial compression is effected. It should be noted that the sealing described in detail with reference to FIGS. 1 and 2 also takes place in the embodiment shown in FIGS. 3 and 4.

While in the foregoing embodiments of the present inventions have been set forth in considerable detail for the purposes of making a complete disclosure of the invention, it may be apparent to those of skill in the art that numerous changes may be made in such detail without departing from the spirit and principles of the invention.

What is claimed is:

1. A high pressure modular liquid chromatography column apparatus utilizing material for separating constituents comprising:
   a. a tube filled with the material said tube having a first end portion and a second end portion;
   b. means for plugging said first end portion of said tube, said plugging means including a passage therethrough, said plugging means fitting adjacent the material within said tube and being movable within said tube;
   c. an end fitting having a portion placed within said tube adjacent said plugging means, said end fitting including a passage therethrough which communicates with said passage of said plugging means;
   d. means for sealing a portion of the inside of said tube between said plugging means and said end fitting, portion within said tube, said sealing means extending along the circumference of said inside of said tube;
   e. means for retaining said end fitting within said tube; and
   f. means for enclosing said second end portion of said tube, said enclosing means including a passage therethrough from the exterior of said tube to the interior thereof.

2. The column apparatus of claim 1 which additionally comprises means for connecting a portion of said plugging means to said end fitting.

3. The column apparatus of claim 2 in which said plugging means includes a stopper having a passage therethrough, said stopper being movable along the inside of said tube and lying adjacent the material.

4. The column apparatus of claim 3 in which said plugging means further includes a seal retainer comprising said portion of said plugging means connected to said end fitting by said connecting means, said seal retainer lying between said sealing means and said stopper, said seal retainer further including a passage therethrough which communicates with said end fitting passage and said stopper passage, said seal retainer being movable along the inside of said tube.

5. The column of claim 4 which further includes a first filter being supported by said stopper and a second filter being supported by said seal retainer.

6. The column apparatus of claim 1 which additionally comprises means for urging said end fitting against said plugging means.

7. The column apparatus of claim 1 in which said tube is a first tube and further comprises a second tube filled with a material, said second tube having first and second end portions, and first and second means for enclosing said first and second end portions respectively, and further comprises a coupler including an element having a first portion fitting and being movable within said second end portion of said first tube, said coupler element further including a second portion fitting and being movable within said first end portion of said second tube, said second tube including first and second passages through said first and second enclosing means respectively which communicate with the material within said second tube, said coupler element including a passage therethrough communicating with said first passage of said first enclosing means of said first end portion of said second tube and with said passage of said enclosing means of said second end portion of said first tube.

8. The column apparatus of claim 7 in which said coupler further comprises means for retaining said first and second portions of said coupler element within said first end portion of said second tube, and within said second end portion of said first tube.

9. The column apparatus of claim 8 in which said coupler additionally comprises means for urging said coupler element against said first enclosing means of said first end portion of said second tube.

10. The column apparatus of claim 9 which includes means for connecting said means for urging said end fitting of said first tube against said plugging means, to said means for urging said coupler element against said first enclosing means of said first end portion of said first tube.

11. A high pressure modular liquid chromatography column apparatus comprising:
   a. a first tube having first and second end portions, each end portion including means for enclosing each end portion, each enclosing means including a passage from the exterior of said tube to the interior of said tube, each of said enclosing means having a portion fitting within each tube and movable therewithin;
   b. a second tube having first and second end portions, each end portion including means for enclosing each end portion, each enclosing means including a passage from the exterior of the tube to the interior of the tube, each of said enclosing means having a portion fitting within each tube and movable therewithin;
   c. a coupler including an element having a first portion fitting and being movable within said second end portion of said first tube adjacent said enclosing means of said second end portion of said first tube, said element further including a second portion fitting and being movable within said first end portion of said second tube adjacent said enclosing means of said first end portion of said second tube, said coupler having a passage therethrough communicating with said passages through said enclosing means of said second end portion of said first tube and said first end portion of said second tube, and said coupler further including means for urging said coupler toward said enclosing means of said first portion of said second tube; and
   d. means for urging said enclosing means of said first portion of said first tube toward said second portion of said first tube.

12. The column apparatus of claim 11 which additionally comprises means for connecting said means for urging said coupler toward said enclosing means of said first portion of said second tube to said means for urging said enclosing means of said first portion of said first tube toward said second portion of said first tube.

13. A liquid chromatography column packed with material comprising:
   a. a tube containing the material, said tube having a first end portion and a second end portion;
   b. a stopper having a passage therethrough, said stopper being movable along the inside of said tube and lying adjacent the material at said first end portion of said tube;
   c. a replaceable filter which lies between said packing material and, at least a portion of said stopper, said replaceable filter being movable within the inside of said tube and being capable of contacting and pressing the material within the tube thereby, and
   d. means for enclosing said second end portion of said tube, said enclosing means including a passage therethrough from the exterior of said tube to the interior thereof.

14. The liquid chromatography column of claim 13 in which said stopper includes a cavity which communicates with said passage through said stopper, and at least a portion of said filter lies within said cavity.

15. A high pressure modular liquid chromatography column utilizing material for separating constituents comprising:
   a. a tube filled with material, said tube having a first end portion, a second end portion, and an inside wall;
   b. means for enclosing said first end portion of said tube, said enclosing means for said first end portion of said tube including a passage therethrough which communicates with the material within said tube, said first enclosing means having at least a part within said tube and being movable within said tube;
   c. means for enclosing said second end portion of said tube, said enclosing means for said second portion of said tube including a passage therethrough communicating with the material within said tube, said second enclosing means having at least a part within said tube, said material being positioned between said first and second enclosing means;
   d. means for circumferentially sealing a portion of the inside of said first and second end portions of said tube between said parts of said first and second enclosing means within said first and second tubes respectively, and said inside wall of said tube; and
   e. means for retaining said parts of said first and second enclosing means within said tube.

16. The high pressure modular liquid chromatography column of claim 15 which additionally comprises means for urging said first enclosing means toward the material within said tube.

* * * * *